United States Patent
Stern

(10) Patent No.: US 11,363,965 B2
(45) Date of Patent: Jun. 21, 2022

(54) SYSTEMS AND METHODS FOR MEASURING AND CHARACTERIZING INTERIOR SURFACES OF LUMINAL STRUCTURES

(71) Applicant: VS Medtech, Inc., Milpitas, CA (US)

(72) Inventor: Roger A. Stern, Cupertino, CA (US)

(73) Assignee: VS Medtech, Inc., Milpitas, CA (US)

( * ) Notice: Subject to any disclaimer, the term of this patent is extended or adjusted under 35 U.S.C. 154(b) by 99 days.

(21) Appl. No.: 16/274,628

(22) Filed: Feb. 13, 2019

(65) Prior Publication Data

US 2019/0175071 A1 Jun. 13, 2019

Related U.S. Application Data

(62) Division of application No. 14/263,698, filed on Apr. 28, 2014, now Pat. No. 10,219,724.

(60) Provisional application No. 61/818,849, filed on May 2, 2013.

(51) Int. Cl.
| | |
|---|---|
| *A61B 5/107* | (2006.01) |
| *A61B 5/00* | (2006.01) |
| *A61B 5/02* | (2006.01) |
| *A61B 5/287* | (2021.01) |

(52) U.S. Cl.
CPC ........ *A61B 5/1076* (2013.01); *A61B 5/02007* (2013.01); *A61B 5/1077* (2013.01); *A61B 5/6853* (2013.01); *A61B 5/0084* (2013.01); *A61B 5/287* (2021.01); *A61B 5/6852* (2013.01)

(58) Field of Classification Search
CPC . A61B 5/1076; A61B 5/6853; A61B 5/02007; A61B 5/1077; A61B 5/6852; A61B 5/0422; A61B 5/0084
See application file for complete search history.

(56) References Cited

U.S. PATENT DOCUMENTS

| | | | |
|---|---|---|---|
| 5,261,904 A | * | 11/1993 | Baker ................ A61B 18/245 606/15 |
| 5,740,808 A | | 4/1998 | Panescu et al. |
| 6,110,200 A | | 8/2000 | Hinnenkamp |
| 6,755,861 B2 | | 6/2004 | Nakao |
| 8,246,628 B2 | | 8/2012 | Rabiner |

(Continued)

FOREIGN PATENT DOCUMENTS

| | | |
|---|---|---|
| CA | 2471106 A1 | 1/1995 |
| JP | H09503677 A | 4/1997 |

(Continued)

OTHER PUBLICATIONS

European search report and opinion dated May 23, 2016 for EP Application No. 14791528.

(Continued)

*Primary Examiner* — Bo Joseph Peng
(74) *Attorney, Agent, or Firm* — Wilson Sonsini Goodrich & Rosati

(57) ABSTRACT

A digital topographic model of the luminal surface is generated by projecting an optical pattern on the luminal surface from the first location within the lumen. At least a portion of the projected pattern is detected from a second location within the lumen which is based apart from the first location. The dimensions of the luminal wall can be measured by triangulation in order to produce the digital topographic model of the body lumen.

19 Claims, 14 Drawing Sheets

(56) References Cited

U.S. PATENT DOCUMENTS

| | | | |
|---|---|---|---|
| 10,219,724 B2 | 3/2019 | Stern | |
| 2002/0068853 A1 | 6/2002 | Adler | |
| 2002/0138075 A1 | 9/2002 | Edwards et al. | |
| 2002/0183729 A1* | 12/2002 | Farr | A61B 18/245 606/15 |
| 2003/0164952 A1 | 9/2003 | Deichmann et al. | |
| 2004/0249267 A1* | 12/2004 | Gilboa | A61B 5/065 600/424 |
| 2005/0014995 A1 | 1/2005 | Amundson et al. | |
| 2005/0075724 A1 | 4/2005 | Svanidze et al. | |
| 2005/0137459 A1* | 6/2005 | Chin | A61B 5/064 600/179 |
| 2005/0228260 A1* | 10/2005 | Burwell | A61N 5/062 600/408 |
| 2007/0078500 A1 | 4/2007 | Ryan et al. | |
| 2007/0244552 A1 | 10/2007 | Salahieh et al. | |
| 2007/0287880 A1 | 12/2007 | Ovil et al. | |
| 2008/0097476 A1 | 4/2008 | Peh et al. | |
| 2008/0275428 A1* | 11/2008 | Tegg | A61M 25/0069 604/533 |
| 2009/0323076 A1 | 12/2009 | Li et al. | |
| 2010/0061873 A1 | 3/2010 | Ikemura | |
| 2010/0081873 A1 | 4/2010 | Tanimura et al. | |
| 2010/0094270 A1 | 4/2010 | Sharma | |
| 2010/0168839 A1 | 7/2010 | Braido et al. | |
| 2010/0191276 A1 | 7/2010 | Lashinski | |
| 2010/0198346 A1 | 8/2010 | Keogh et al. | |
| 2010/0249601 A1 | 9/2010 | Courtney | |
| 2011/0057930 A1 | 3/2011 | Keller et al. | |
| 2011/0098602 A1 | 4/2011 | Campbell et al. | |
| 2011/0237940 A1 | 9/2011 | Raleigh | |
| 2011/0276127 A1 | 11/2011 | Forster et al. | |
| 2011/0301418 A1 | 12/2011 | Gharib et al. | |
| 2012/0065729 A1 | 3/2012 | Pintor et al. | |
| 2012/0092461 A1 | 4/2012 | Fisker et al. | |
| 2012/0289982 A1 | 11/2012 | Gunday et al. | |
| 2013/0006231 A1 | 1/2013 | Sharma et al. | |

FOREIGN PATENT DOCUMENTS

| | | |
|---|---|---|
| JP | 2007285891 A | 11/2007 |
| JP | 2013506861 A | 2/2013 |
| JP | 6358135 B2 | 7/2018 |
| WO | WO-9501751 A1 | 1/1995 |
| WO | WO-0103599 A2 | 1/2001 |
| WO | WO-2009032016 A1 | 3/2009 |
| WO | WO-2014179775 A1 | 11/2014 |

OTHER PUBLICATIONS

Office Action dated Dec. 23, 2016 for U.S. Appl. No. 14/263,698.
EP14791528.4 Communication pursuant to Article 94(3) EPC dated Nov. 2, 2021.
PCT/US2014/036702 International Search Reports Written Opinion of the International Searching Authority dated Oct. 7, 2014.
U.S. Appl. No. 14/263,698.Office Action dated Sep. 26, 2017.

* cited by examiner

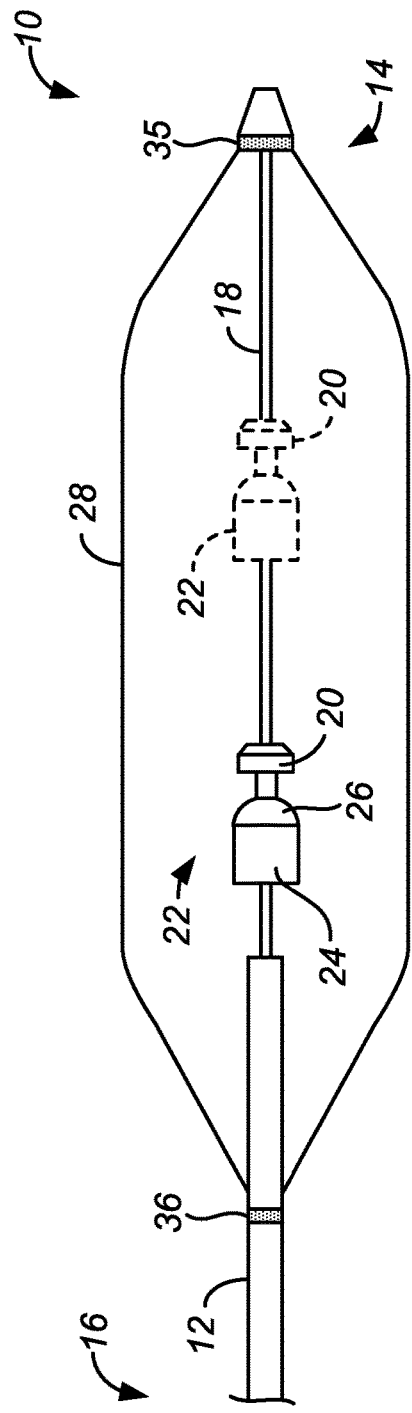
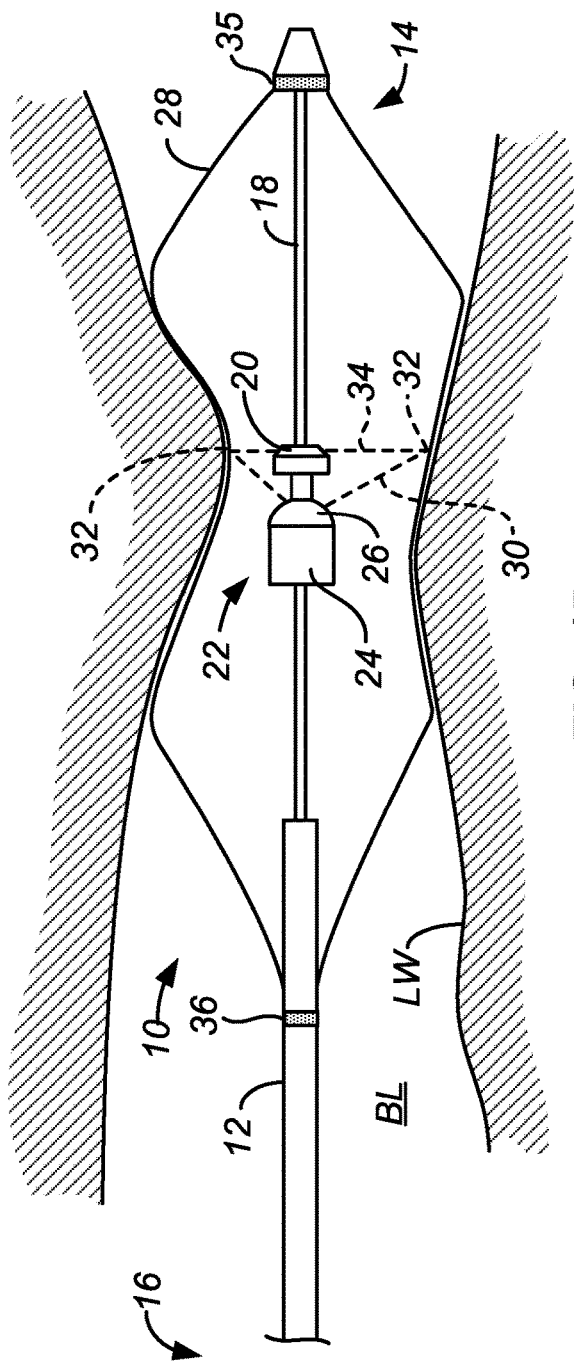
FIG. 1A
FIG. 1B

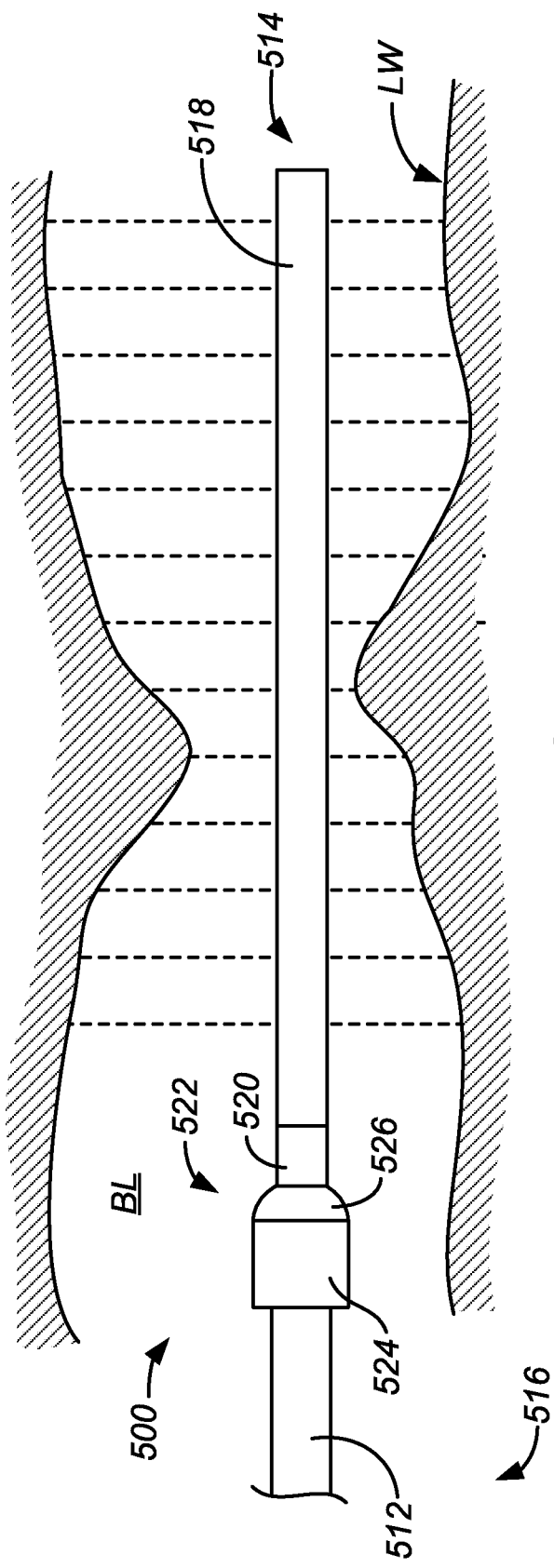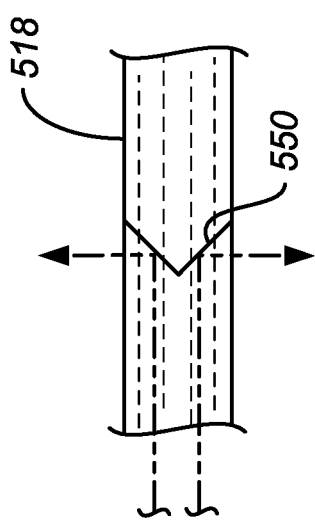
FIG. 5A
FIG. 5B

SYSTEMS AND METHODS FOR MEASURING AND CHARACTERIZING INTERIOR SURFACES OF LUMINAL STRUCTURES

CROSS-REFERENCE TO RELATED APPLICATIONS

This application is a divisional of U.S. patent application Ser. No. 14/263,698, filed Apr. 28, 2014, which claims the benefit of U.S. Provisional Application No. 61/818,849, filed May 2, 2013, the entire content of which is incorporated herein by reference.

BACKGROUND OF THE INVENTIONS

1. Field of the Invention

The present invention relates generally to medical devices and methods. More particularly, the present invention relates to systems and methods for optically scanning an interior surface of a body lumen to generate digital dimensional information relating to a lumen surface.

Minimally invasive implantation of vascular and other luminal prostheses has become widespread in the last ten years. The intravascular delivery and implantation of stent grafts for treating abdominal and other aneurysms is now common place for patients at risk for receiving open surgical implantation procedures. The percutaneous delivery and implantation of prosthetic aortic valves has recently become available and is quickly becoming a preferred treatment option for patients at risk for receiving open heart surgery. Both of these procedures, and other percutaneous therapeutic procedures, would benefit from characterization of the site of implantation prior to choosing the implant and performing the implantation procedure. Presently, external imaging, such as CT and MRI, is the most common technique for obtaining anatomical information regarding the implantation site. CT and MRI, however, provide limited dimensional information. The images which are obtained must be interpreted in order to derive dimensional information which is often inaccurate.

Intravascular ultrasound imaging (IVUS) can also be used to characterize aneurismal and valve replacement sites prior to implantation procedures. The IVUS probes are intravascularly placed within the blood vessel or heart. While the ultrasonic images may be improvements over those obtained by external scans, the images still lack the dimensional detail which would be desirable for selecting a prosthesis for subsequent implantation. These images also suffer from artifacts which make it difficult to interpret the anatomical boundaries of the structures, further leading to inaccuracy in determining dimensions.

A further shortcoming of both the external and internal imaging modalities is an inability to measure the luminal area and anatomical dimensions when the body lumen is under deformational stress equivalent to that provided by the prosthetic implant. For example, when planning the implantation of a prosthetic heart value, it would be useful to determine the dimensions of the valve annulus and surrounding tissues while the annulus was placed under a radially expansive force equivalent to that provided by the prosthetic implant. The conventionally utilized imaging methodologies do not allow measurement of the annulus diameter which would be assumed after a prosthetic device is deployed.

For these reasons, it would be desirable to provide improved methods, devices, and systems for obtaining dimensional information regarding an implantation site in a body lumen prior to actual implantation of a prosthesis. It would be particularly desirable if the dimensional information could be measured directly, not indirectly through image interpretation, and if the measurements could be made while the luminal site is under a stress or other deformational force which is analogous or equivalent to that which would be provided by the implant after implantation. It would be further desirable if the methods, devices and systems used for obtaining the measurement information could also obtain other information, such as color or other characteristics of the tissue being scanned during measurement. At least some of these objectives will be met by the inventions described below.

2. Description of the Background Art

Balloons and other devices for sizing valve annuluses and other lumens are described in U.S. Pat. Nos. 6,110,200; 6,755,861; and 8,246,628 and in U.S. Patent Publ. Nos. US2012/289982; US2012/065729; US2011/276127; US2011/237940; US2011/098602; US2010/198346; US2010/168839; US2007/244552; and US2005/075724.

SUMMARY OF THE INVENTION

The present invention provides methods, devices and systems for directly measuring dimensions and other characteristics of a luminal structure in a patient body. As used hereinafter and in the claims, the phrase "luminal structure" refers to all body lumens, passages, open body cavities, closed body cavities and the like, specifically including heart valve annuluses, aneurysms, left atrial appendages, and vascular lumens (particularly including occluded regions of the vasculature), including prosthetic implants implanted in such structures, such as stents, stent grafts, heart valves and the like. In particular, the present invention provides for direct measurement of a lateral or radial dimension(s) of a body lumen over a discrete axial length of the lumen. Dimensions will be acquired using optical tools and will be typically be calculated based on the relative positions of an illumination source within the body lumen and a light sensor also in the body lumen but spaced-apart from the illumination source. The illumination source projects a pattern of light over a region of the lumen wall to be measured, and the lateral or radial dimensions can be calculated using triangulation. The dimension may be determined in a variety of ways, but will usually be acquired as points or lines in a three-dimensional space using conventional radial or Cartesian coordinate systems. The dimensional information is usually provided in digital files, and the digital files can be represented as wire frame, solid or other conventional images on a display screen. The resulting dimensionally accurate images may then be overlaid with dimensionally accurate images of a prosthetic device intended to be implanted. The physician or the user can then visually determine the adequacy of the intended implant. Alternatively or additionally, checking algorithms can be used to assess fit of the prosthesis. Such dimensional information, however, is useful in many other circumstances, such as in the sizing and design of custom implants which can be made to precisely match the anatomical dimensions of the target body lumen or other anatomical space.

The present invention will typically utilize optical probes and tools for the direct measurement and characterization of an inner wall or other interior structure of the body lumen. Usually, an optical pattern is projected on the wall where the pattern may be stationary or scanned over the wall. The pattern may be projected directly onto a luminal wall, but will more usually be projected onto or through an inner wall of a balloon or other conformable structure which has been deployed within the target body lumen. The balloon may be elastic so that it inflates and conforms to the interior surface of the luminal wall. Alternative, the balloon may be inelastic but oversized so that it will conform to the luminal wall with folding where excess balloon material exists.

The probes and tools of the present invention will typically include at least one illumination source and at least one light sensor to capture the light from the illumination source after it has been reflected from the luminal wall or interior of a balloon. A complete pattern may be projected from the illumination source to cover all or a major portion of the luminal wall with a known geometry so that the light sensor can determine the elevation angles of different points, lines or other components of the pattern, allowing the radial dimension of the wall at any particular point on the pattern to be calculated by triangulation. More usually, however, point, line, ring or other discrete optical pattern will be projected from the illumination source, and light from the illumination source will be physically or electronically scanned over the interior surface of the body lumen or balloon. The probe or tool, typically in the form of a catheter, will be connected to deliver analog or digital data to a computer or other processor which in turn can generate three-dimensional models of the luminal wall geometry of the body lumen. Typically, the processor may utilize finite element modeling (FEM) techniques in calculating the three-dimensional models when considering the change in geometry due to deformational forces.

The catheters utilized in the present invention may have generally conventional structures as needed to reach their target anatomy. For example, the bodies of the catheters intended to measure the dimensions of an aortic valve annulus will be structured to be introduced to the annulus, typically by the same route as intended for the subsequent implementation. Thus, the catheters can be structured to be introduced into the femoral artery and over the aortic arch. Alternatively, the catheters may be structured to be advanced transapically into the heart and aortic valve annulus. Catheters intended for imaging an abdominal aortic aneurysm (AAA) will typically be configured to be introduced into a femoral artery and upward into the abdominal aorta. Catheters may also be configured for introduction through laparoscopic, thoracoscopic, or other known techniques for introducing catheters and probes into the body.

The catheters of the present invention may be configured for direct scanning and measurement of the body luminal where the illumination source and light sensor are mounted at or near a distal portion of the catheter in such a way that they may be directly exposed within the body lumen. More typically, however, the catheters will include an inflatable structure, e.g. a balloon, configured to cover the illumination source and light sensor during use. In particular, when the catheters are intended to be used in a vascular environment, where blood can obscure optical measurements, it will be useful to provide an optically transparent environment surrounding the illumination source and the light sensor so that the pattern may be projected and detected without interference. By inflating a balloon with such an optically transparent medium, the optically transparent environment can be easily obtained. By optically transparent, it is meant that the medium will allow light of a preselected wave length (or wave lengths) to be transmitted, reflected and detected within the luminal environment without substantial interference or attenuation.

Alternatively, at least a distal portion of a catheter body could be formed from an optically transparent material that allows the passage of light through the catheter body wall as defined above. The illumination source and light sensor can then be placed in an interior passage or lumen within the transparent distal portion of the catheter body to scan the luminal wall. As the catheter body will usually not be expandable, in some instances in may be desirable or necessary to clear the optical field surrounding the transparent section of the catheter body with a fluid that allows the passage of light as will be described in greater detail below.

When using a balloon, the balloon will typically be inflated to conform to the interior surface of the luminal structure. The balloon can be highly compliant and "elastically" conform to the structure. Alternatively, the balloon can be inelastic or non-compliant but have a larger width or transverse dimension than the body lumen to be measured. Excess balloon material will simply fold over or be compacted after the balloon is fully inflated. In either case, the balloon inflation pressure may be set relatively low so that the balloon will conform to the interior of the luminal structure with little or no deformation of the lumen. Alternatively, the balloon can be inflated to higher pressures which cause deformation (expansion) of the luminal wall. Such higher pressure inflation can allow estimation of the luminal wall dimensions after implantation of a particular device, such as a stent, valve, or other device which will apply a radially outward force against the luminal wall. By inflating the balloon to a pressure which is generally equivalent to the expected expansive force of the implanted prosthesis, the dimensions of the lumen after deployment of the prosthesis can be accurately predicted.

The balloons utilized in the catheters of the present invention may be transparent, in which case all or at least a portion of the light from the illumination source will reflect from the inner wall of the body lumen. Alternatively, the balloon can be opaque and/or have a moderately or highly reflective inner surface. In the latter cases, at least a portion of light from the illumination source will reflect from the interior of the balloon wall.

Once the catheter or other probe has been deployed and the balloon has optionally been inflated, the illumination source is energized to project a pattern on the interior surface of either the luminal wall or the balloon. The light sensor(s) detect the projected optical pattern including the apparent angle or elevation of points, lines or the portions of the optical pattern relative to the light sensor. Using the known position and geometry of the projected optical pattern and the angle or elevation of the observed reflected light, the dimensions of the optical pattern can be calculated. As the optical pattern is present at or near the interior wall of the body lumen, the calculated dimensions in geometry are equivalent to the dimensions of the body walls at the time the measurements are made.

When the projected light is reflected directly from a luminal wall or through a transparent balloon, the color and/or florescent content of the reflected or emitted light can be analyzed to yield information regarding the tissue composition. For example, if white light is projected and red light is received, it will be apparent that the tissue is red. Similarly, reflected yellow light or white light will tell the physician that the luminal wall is yellow or white, respectively. In other instances, non-white light can be used as the illumination source in order to determine other characteristics of the tissue, such as tissue fluorescence, and the like. Such color information can be useful, for example, in detecting the presence of vulnerable plaque in the vasculature.

In a first aspect of the present invention, a method for generating a digital topographic model of a luminal surface of the body lumen comprises projecting an optical pattern on the luminal surface from a first location within the body lumen. At least a portion of the light reflected from the projected pattern is detected from a second location within the lumen where the second location is spaced-apart from the first location. The digital topographic model is then generated by triangulating the detected pattern from the projection and detection locations. For example, triangulation can be based on determining projection and detection angles and calculating the radius of the lumen based on the distance between the first and second locations.

In specific embodiments, projecting comprises projecting light from at least one illumination source located within the lumen. Optionally, the illumination source may be translated along a path through the lumen in order to scan the projected pattern over the luminal wall. The translation path will extend over a "characterization" distance or length of interest within the body lumen, typically in a range from 5 mm to 250 mm, usually from 10 mm to 150 mm, with specific distances set forth below for different body lumens. The specific length of the translation path will depend heavily on what luminal structure is being measured and for what purpose. An aortic valve annulus would usually require a different characterization length than would an aortic abdominal aneurysm (AAA), a left atrial appendage, a region of the vasculature, or the like. Specific exemplary characterization lengths are set forth in Table 1 below for different anatomies. The projected pattern may have a variety of geometries but will often be a circular or ring pattern which circumscribes a cross-section of the lumen. By advancing such a ring or circle pattern axially through the lumen, the cross-sectional dimensions of the body lumen can be calculated over the scanned length.

TABLE 1

Exemplary Characterization Lengths

| Anatomical Site | Characterization Length Max/Min | Diameter of Lumen Min/Max |
|---|---|---|
| Aortic valve Complex | 30 mm-50 mm | 20 mm-40 mm |
| Illiac arteries | 160 mm-250 mm | 5 mm-20 mm |
| Abdominal aortic Aneurysm | 10 mm-250 mm | 10 mm-30 mm |
| Left Atrial appendage | 20 mm-50 mm | 5 mm-15 mm |
| Vasculature | 5 mm-150 mm | 3 mm-20 mm |

Typically, detecting at least a portion of the projected pattern will comprise sensing light from the illumination source reflected from the luminal wall and/or balloon interior with at least one light sensor position within the lumen. The light from the illumination source will have been reflected from the wall so that the sensor will observe the apparent position of the projected light on the wall when it is struck by the light. The sensor may be a CCD, CMOS, or other array detector which can determine the location of pixels which detect the light. Using such technologies, the angles of incidence of light across the sensor and associated lenses may be calculated.

In specific embodiments, the light sensor may be coupled to the illumination source so that they may be translated in tandem through the lumen. By coupling the light sensor at a fixed distance to an illumination source that projects a ring of light radially outward, preferably at a perpendicular angle relative to an axis of travel, triangulation can be readily achieved based on the detected angle of the light sensed by the light sensor.

In another specific embodiment, at least one light sensor may remain stationary while the illumination source is translated through the lumen. The illumination source will typically project a ring pattern radially outwardly at an angle perpendicular to the axis of travel. The fixed light sensor can track the angle of incidence of the reflected light as the distance between the sensor and the illumination source changes and is tracked.

In still another specific embodiment, the illumination source includes a plurality of individual illumination sources which are distributed along a path through lumen. Usually, but not necessarily, the distributed illumination sources will be fixed and will not move relative to each other or to the light detector(s). Alternatively, it would be possible to move some or all of the plurality of illumination sources although that would generally not be preferred. The plurality of illumination sources will typically extend over a characterization distance in the range from 5 mm to 250 mm, usually from 10 mm to 150 mm, with specific ranges for different anatomies being set forth in Table 1 above. The illumination sources will typically project a ring pattern which circumscribes a cross-section of the lumen surrounding the source in a manner similar to the axially translating illumination sources. In other instances, at least some of the plurality of illumination sources may project patterns which are geometrically different from one or more patterns projected by others of the illumination sources. Additionally, in some instances, at least some of the plurality of illumination sources will project a pattern having a different light wavelength than those projected by one or more of the other illumination sources.

In still further aspects of the methods of the present invention, an illumination source and a light detector may be coupled together, usually at a fixed distance, and the resulting assembly drawn through a body lumen, optionally over a guidewire or other guiding element. The illumination source will typically project a circumferential ring, and the light detector will measure the reflection angles which in turn can be used to triangulate the radial distance to the luminal wall surface (based on the known usually fixed distance between the illumination source and the light detector) circumferentially at all points over the length through which the catheter is drawn.

Detecting the reflected light will typically comprise sensing light from the at least one illumination source, where the light from the illumination source is first reflected from the wall and/or an inner balloon surface within the lumen. In some embodiments, a single light sensor may be utilized where the single light sensor may be located at one end of one or more illumination sources. In other instances, two or more light sensors may be utilized where at least one light sensor will be at one end of the illumination source(s) and a second illumination source will be at another end of the plurality of illumination sources. The use of addition light sensors will increase the field of view of the light sensors thus allowing increased coverage of the luminal wall and/or increased accuracy.

As used herein and in the claims, the phrase "luminal surface" will include both a fully exposed luminal surface free from covering structures as well as a luminal surface which is covered by a balloon structure or other membrane. Usually, such balloon structures or other membranes will conform to the luminal walls so that the contours and geometries of the luminal wall will be imparted to the balloon or lumen surface. Frequently, the methods of the present invention will comprise inflating a balloon within a body lumen so that the balloon conforms to the luminal surface. As described above, the balloon may be elastic or inelastic, and the light from the illumination source may be reflected from the inner wall of the balloon. Alternatively, when the balloon is transparent to at least a portion of the illumination wavelength, the illumination light may penetrate through the balloon and be reflected directly from the luminal wall. When the balloon is not transparent, it will usually have an inner surface with enhanced reflectivity, for example being coated with a material which enhances specular reflection.

Methods of the present invention are suitable for generating digital topographic models of virtually any human or animal body lumen but will be particularly useful for modeling heart valve annuluses, aneurysms, vascular occlusions, and the like. In particular, the methods are useful for determining the topographic models of aortic valve annuluses prior to prosthetic valve implantation and for determining the topographic models of abdominal aortic aneurysms prior to implantation of stent grafts or other procedures.

While the methods of the present invention are particularly useful for the determination of topographic models, the methods are also useful for analyzing the nature of the luminal wall being scanned. For example, the wavelength or other optical properties of the light and/or fluorescence reflected or emitted from the luminal wall may be analyzed in the order to determine some wall characteristic, such as the nature of occlusive or diseased materials in a blood vessel. In specific incidences, the projected light may comprise two or more different wavelengths allowing simultaneous analysis of different properties specific to each of the wavelengths.

In a second aspect, the present invention provides catheters and devices for scanning a luminal surface of a body lumen to generate electronic signals useful for providing a digital topographic model of the luminal surface. Such catheters comprise a catheter shaft having a distal end and a proximal end. At least one illumination source is mounted at or near a distal portion of the catheter shaft. The illumination source is typically configured to project an optical pattern onto the luminal wall when the distal portion of the catheter is in the body lumen. At least one sensor is mounted on or near the distal portion of the catheter at a location spaced-apart from the location of the illumination source. This sensor is configured to sense light from the illumination source which has been reflected from the luminal wall and to produce an electronic signal representative of the reflected light pattern. The digital topographic model can be generated by triangulation based upon the projected optical pattern, a distance between the illumination source and the sensor, and the electronic signal, where the electronic signal typically includes information representing the angles and elevations of both the light projected from the illumination source and the light detected by the light sensor.

In a first embodiment, the at least one illumination source is mounted to axially translate over the distal portion of the catheter shaft. Typically, the at least one illumination source will be able to translate over a distance in the range from 5 mm to 250 mm, usually from 10 mm to 150 mm, with specific ranges for different anatomies being set forth in Table 1 above. The illumination source may project a wide variety of specific patterns, with a ring pattern often being employed.

The at least one light sensor will typically be coupled to the illumination source so that the light sensor is able to translate in tandem with the illumination source. Such coupling will provide a fixed distance between the illumination source and light sensor in order to simplify the triangulation calculations.

In other specific embodiments, the at least one light sensor may be fixedly mounted on the distal portion of the shaft, usually being on a proximal or distal side of the at least one illumination source. Often, at least a second light sensor will also be fixedly mounted on the shaft, most often on the other side of the at least one illumination source. In this way, the at least one illumination source may translate between the two fixed light sensors in order to provide for improved tracking of the projected light pattern.

In still other embodiments, a plurality of illumination sources may be distributed over the distal portion of the shaft. The plurality of illumination sources may be distributed over a distance in distance in the range from 5 mm to 250 mm, usually from 10 mm to 150 mm, with specific ranges for different anatomies being set forth in Table 1 above. Typically, at least some of the plurality of illumination sources will project a ring pattern which circumscribes a cross-section of the lumen surrounding the source, although a variety of other illumination sources would also be available. The plurality of illumination sources may all project the same pattern or at least certain ones of the illumination sources may project patterns which are different than others of the illumination sources. Similarly, the plurality of illumination sources may project light of the same wavelength or individual ones of the light illumination sources may project light having different wavelengths than that projected by others of the illumination sources.

Usually, although not necessarily, an inflatable balloon will be secured to the shaft over the illumination source and the light sensor in order to isolate the illumination source in the light's sensor from the luminal environment. The balloon may be elastic or inelastic, but will in at least most cases conform to the luminal wall when inflated within the body lumen. The balloon may have a reflective interior surface or may be fully or partially transparent in order to allow light from the illumination source to penetrate the balloon and reach the luminal wall.

The catheters of the present invention may be incorporated into systems comprising the catheter in combination with a processor connected to receive the electronic signal from the catheter. The processor will typically be configured to generate the digital topographic model by triangulation based upon the projected optical pattern and the distance between the illumination source and the sensor. The processor may also be able to analyze color and other characteristics of the reflected light detected by the light sensor, where the light or other characteristics may be diagnostic of luminal conditions, such as the nature of plaque within a diseased blood vessel.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIGS. 1A-1C illustrate a first embodiment of a catheter constructed in accordance with the principles of the present invention where an illumination source and a light sensor are mounted to axially translate in tandem within a conformable balloon.

FIG. 2 shows the catheter in a luminal environment without a stent and FIG. 2A shows the catheter in a luminal environment with a stent.

FIGS. 5A and 5B illustrate a fifth embodiment of a catheter constructed in accordance with the principles of the present invention, where an illumination source comprises a plurality of partially reflective mirrors disposed along a light conduit with a single light sensor at one end of the illumination sources with no balloon.

DETAILED DESCRIPTION OF THE INVENTION

Figure 1C:
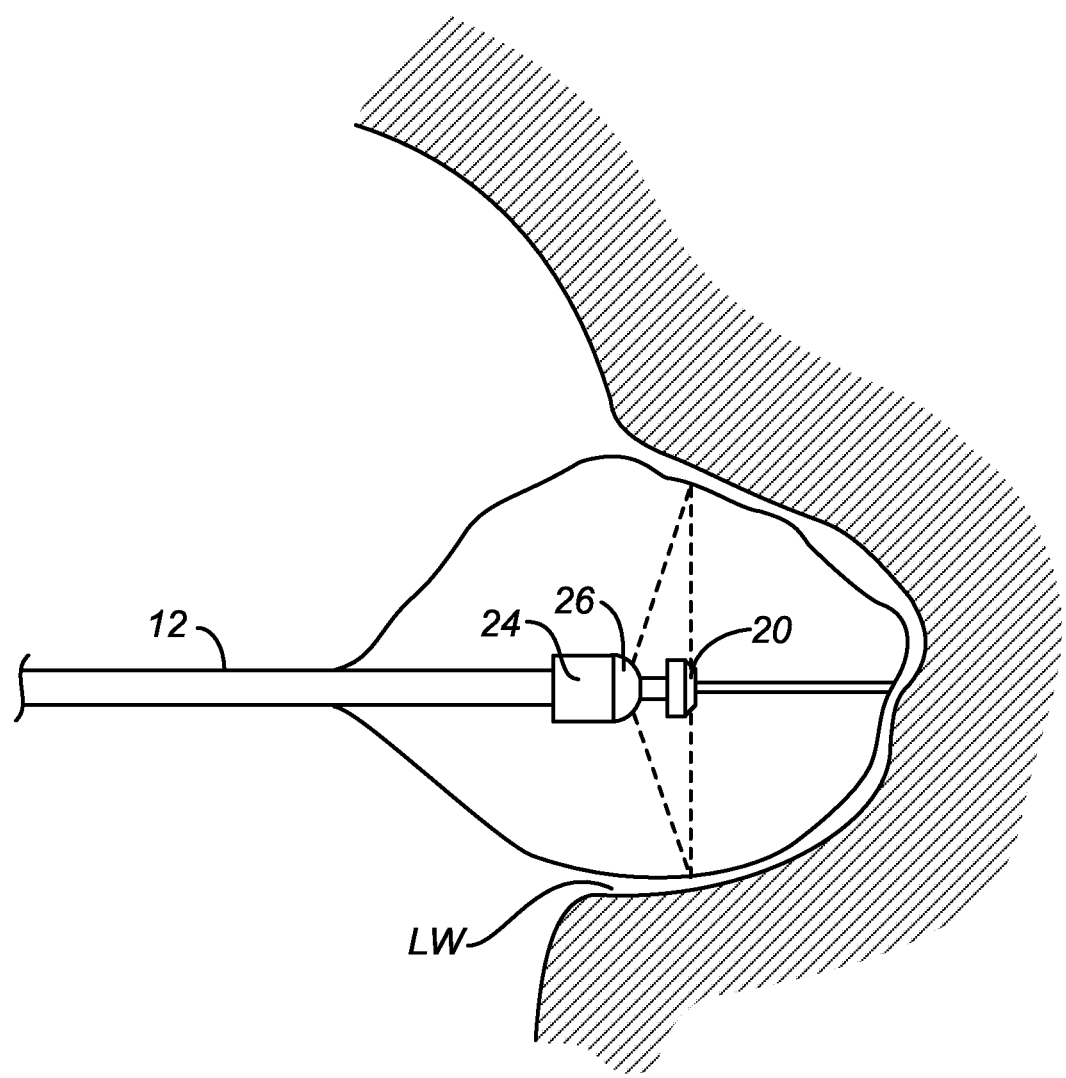

Referring to FIGS. 1A and 1B, a catheter 10 having a shaft 12 with a distal end 14 and proximal end 16 is illustrated and will be described. A distal portion 18 of the shaft 12 is configured to carry an illumination source 20 and a light sensor 22, both which are adapted to axially translate over the distal portion 18. Typically, the illumination source 20 and light sensor 22 will be coupled so that they will travel in tandem as illustrated, for example, in broken line in FIG. 1A. The light sensor 22 typically comprises a camera 24 such as a charge coupled device (CCD) sensor, a complementary metal-oxide-semiconductor (CMOS) sensor, an N-type metal-oxide-semiconductor (NMOS) sensor, or other solid state camera component, and a lens 26, such as a wide angle or "fish eye" lens, a pinhole lens, or the like. The lens 26 and camera 24 are arranged so that they can detect light which strikes an inside surface of the lumen 28 which is disposed around the distal portion 18 of the catheter 10.

The catheter can also optionally have a plurality of electrogram sensing electrodes 35, 36. The electrodes 35, 36 are particularly useful for positioning the balloon within the aortic valve annulus and for assessing the region around the aortic valve annulus prior to aortic valve replacement procedures. The electrodes 35, 36 also allow monitoring of changes in a patient's electrogram as pressure is applied to the aortic valve annulus by the balloon. Abnormal changes to the electrogram could indicate the likelihood of heart block after valve replacement, if the replacement valve exerts too much pressure on the aortic annulus.

As shown in FIG. 1B, the illumination source 20 will typically project a ring of light radially outward, as indicate by broken line 30 so that the lens 26 and camera 24 can detect the point 32 where the projected ring of light strikes the inner wall of balloon 28 along a circumferential line 34. As described in more detail below, the angle at which the lens and camera detect the location 32 at which the light strikes the balloon wall and the distance between the camera and the illumination source can be relied on to measure the radial distance outward from the illumination source to the wall of the balloon (and thus the wall of the body lumen) by well-known triangulation calculations. It will be appreciated, of course, that generally the radial distance will depend on the circumferential location of the point along the inner wall of the balloon and the body lumen. Thus, point or location 32' will generally be at a different radial distance than point 32 so that the viewing angle from the lens 26 and camera 24 will differ. The same catheter is useful for scanning a closed ended body cavity, such as a left atrial appendage as illustrated in FIG. 1C.

Figure 1D:
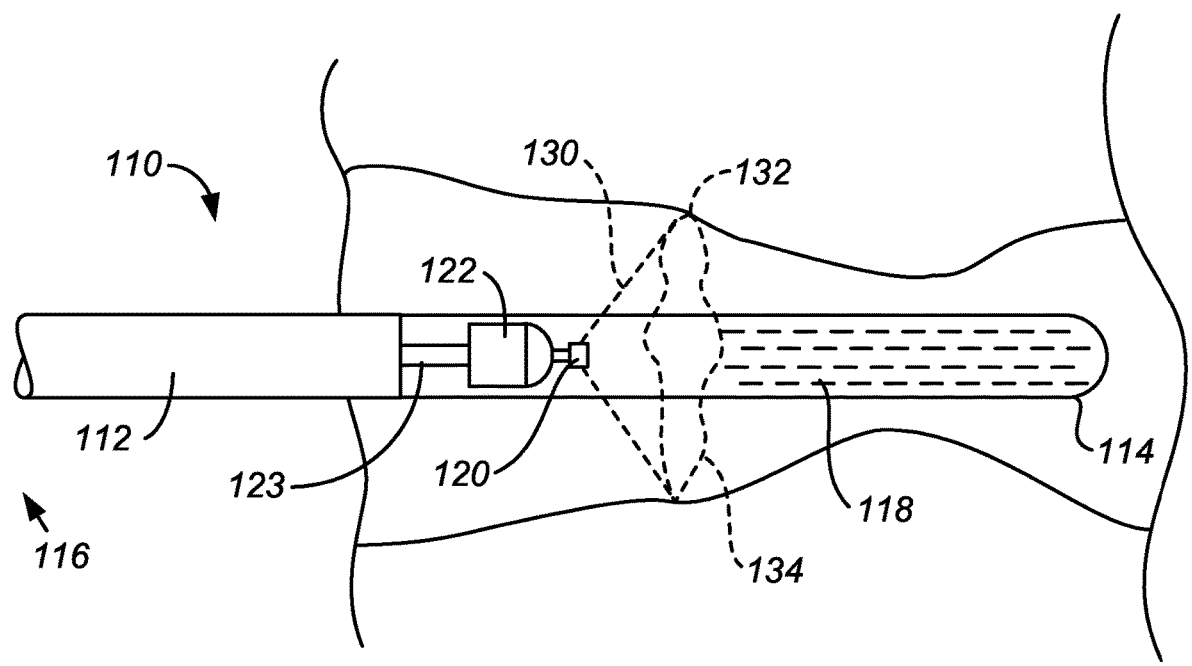
FIG. 1D illustrates a modified first embodiment of a catheter constructed in accordance with the principles of the present invention where an illumination source and a light sensor are mounted to axially translate in tandem within a transparent cylindrical extension of the catheter shaft.

As shown in FIG. 1D, the catheter 10 of FIGS. 1A-1C may be modified to operate without a balloon. A catheter 110 having a catheter body 112 has a distal end 114 and a proximal end 116. Instead of a balloon, a distal portion 118 of the catheter body 112 is transparent and configured to reciprocatably carry an illumination source 120 and a light sensor 122 in an interior passage or lumen thereof. Typically, the illumination source 120 and light sensor 122 are carried by a reciprocatable shaft 123 so that they will travel in tandem similarly to the source and sensor in the embodiment of FIGS. 1A-1C. The path of travel, however, is by the interior passage or lumen of the distal portion 118 rather than by a central shaft, i.e. no central "rail" is needed to guide the illumination source 120 and light sensor 122 although one could optionally be provided. The light sensor 122 typically comprises a camera 124 such as a charge coupled device (CCD) sensor, a complementary metal-oxide-semiconductor (CMOS) sensor, an N-type metal-oxide-semiconductor (NMOS) sensor, or other solid state camera component, and a lens 126, such as a wide angle or "fish eye" lens, a pinhole lens, or the like. The lens 126 and camera 124 are arranged so that they can detect light which passes through the transparent distal section 123 of the catheter shaft and strikes an inside surface of the valve, blood vessel or other luminal surface.

The illumination source 120 will typically project a ring of light radially outward, as indicate by broken line 130 so that the lens 126 and camera 124 can detect the point 132 where the projected ring of light strikes the inner luminal wall of along a circumferential line 34. As described in more detail below, the angle at which the lens and camera detect the location 132 at which the light strikes the balloon wall and the distance between the camera and the illumination source can be relied on to measure the radial distance outward from the illumination source to the wall of the balloon (and thus the wall of the body lumen) by well-known triangulation calculations. As the camera 124 and lens 126 axially scan the luminal wall, the topography of a desired axial length of the lumen can be obtained as described above for the embodiments of FIGS. 1A-1C.

When operating without a balloon, blood plasma or another clear fluid (such as saline or a carbon dioxide) may be injected into the visual field surrounding the distal portion 118 of the catheter to clear the visual field. The need to clear the visual field will depend on the body fluids expected to be surrounding the catheter and the wavelength of the illumination source. For the mouth, esophagus, sinuses, and the like, clearing the visual field may be unnecessary. For the stomach, a gas such as carbon dioxide may be sufficient. In blood vessels and valves, blood plasma, saline, or the like could be used, although near infrared light (750 nm to 1400 nm) could be used to penetrate through blood with less absorption than at visible wavelengths. Near infrared wavelengths could be especially useful when examining relatively small blood vessels (as described below with reference to FIGS. 7A-7C) as the distance the light would need to travel through blood would be short.

Figure 2:
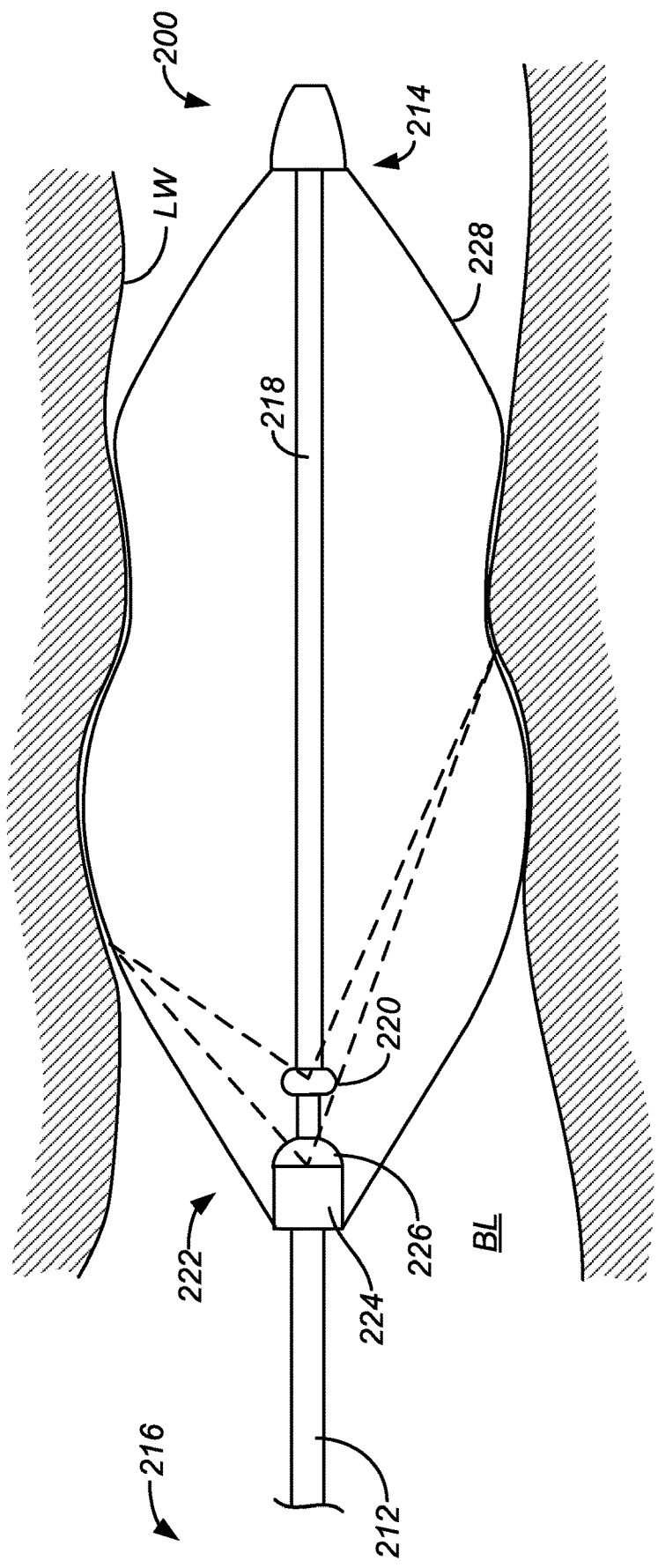
FIGS. 2 and 2A illustrates a second embodiment of a catheter constructed in accordance with the principles of the present invention, where an illumination source is mounted to axially translate within a balloon and a single light sensor is fixed to a shaft of the catheter on one side of the translatable illumination source.

Referring now to FIG. 2, a catheter 200 comprising a catheter shaft 212 having a distal end 214 and a proximal end 216 will be described. A light sensor 222 comprising a camera 224 and lens 226 is fixedly secured at one end of a distal portion 218 attached to the catheter shaft 212. An illumination source 220 is mounted on the distal portion 218 at a location distal to the light sensor 222. In this embodiment, the light sensor 222 will also be fixed on the distal portion 218, and the illumination source 220 will be configured so that it can project light distally forward (and optionally proximally backward) from the location at which it is attached. Thus, the illumination source 220 may project rings, points, lines, or other light patterns at different locations along the inner surface of balloon 228. The radial distance of any such ring, line, or point may then be calculated based on the angle at which the light beam pattern is projected and the angle at which it is detected by the light sensor 222. As the distance between the illumination source 220 and the light sensor 222 is fixed, the radial distance of the point at which the light is striking the balloon may be calculated by conventional triangulation.

Figure 2A:
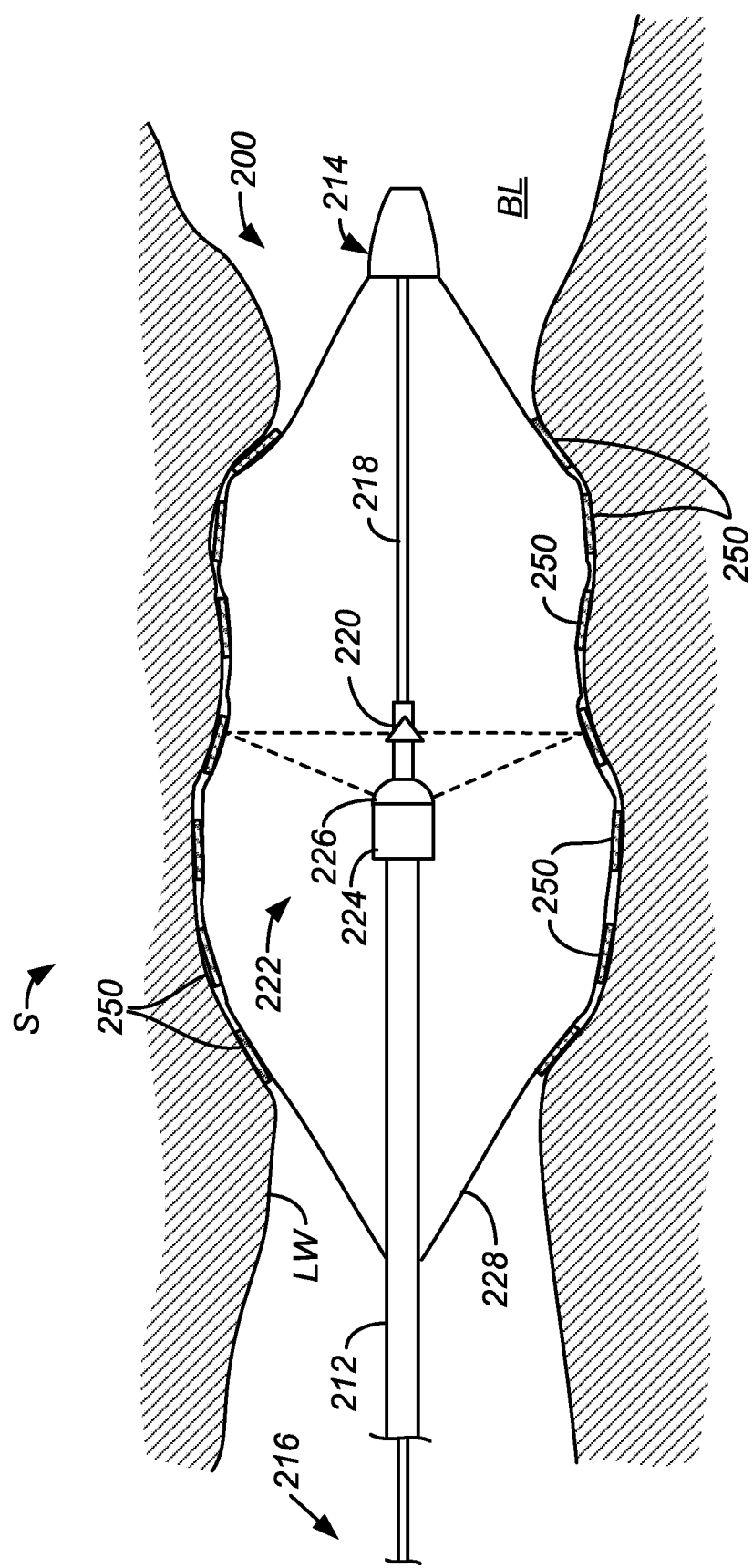

FIG. 2A is similar to FIG. 2 but further illustrates a stent S having a plurality of struts 250 lying against the luminal wall LW. The imaging system of catheter 200 will be able to clearly delineate the location of the stent struts on the luminal wall. Other embodiments of the catheters of the present invention will also be capable of imaging stents and other previously or concurrently placed luminal implants.

Figure 3:
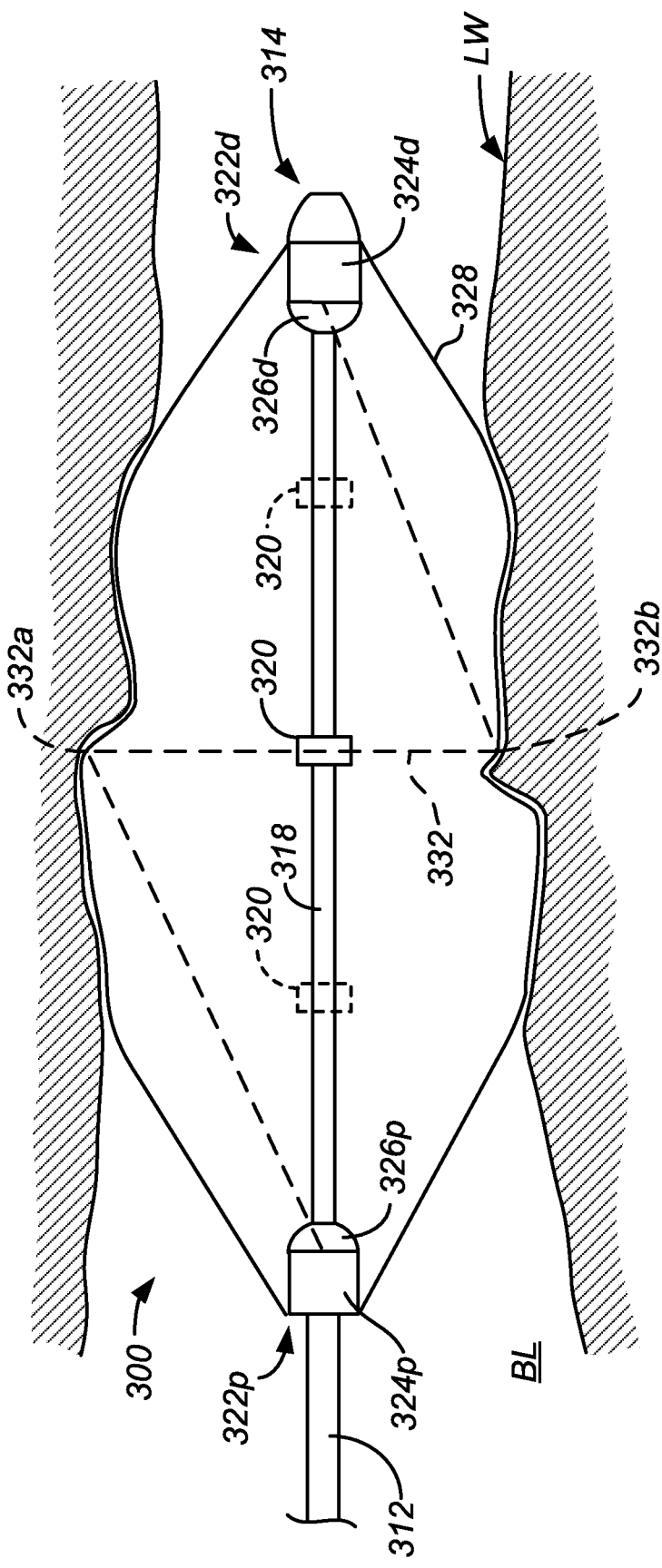
FIG. 3 illustrates a third embodiment of a catheter constructed in accordance with the principles of the present invention, wherein an illumination source is mounted to axially translate between a pair of light sensors within a balloon.

Referring now to FIG. 3, a catheter 300 represents a third embodiment of the present invention. The catheter 300 includes a catheter shaft 312 having a distal end 314 and proximal end 316. A distal portion 318 of the catheter is attached to the catheter shaft 312 and extends distally therefrom. A single illumination source 320 is adapted to axially translate along an axis of the distal portion 318 and is shown in full line at travel midpoint of and in broken line at proximal and distal travel positions.

A proximal light sensor 322p includes both a camera 324p and a lens 326p, and a distal light sensor 322d also includes both a camera 324d and a lens 326d. The illumination source 320 will typically project a ring-shaped light pattern normal to the axis of travel which will illuminate a generally ring pattern 332 on the inner surface of the balloon 328. At many locations, the point of illumination may be detectable from both the proximal light sensor 322p and the distal light sensor 322d. An advantage of having two light sensors, however, is that in certain locations the point of illumination will be detectable only by one of the light sensors. For example, the illumination point 332a may be clearly observed by the proximal light sensor 322p, but would be blocked by the anatomy from the distal light sensor 322d. Similarly, the illumination point 332b may be clearly observed by the distal light sensor 322d but would be blocked by the anatomy from being observed by the proximal light sensor 322p. The illumination sources 420a-420f may also be of different wavelengths or project distinct patterns if illuminated simultaneously.

Figure 4:
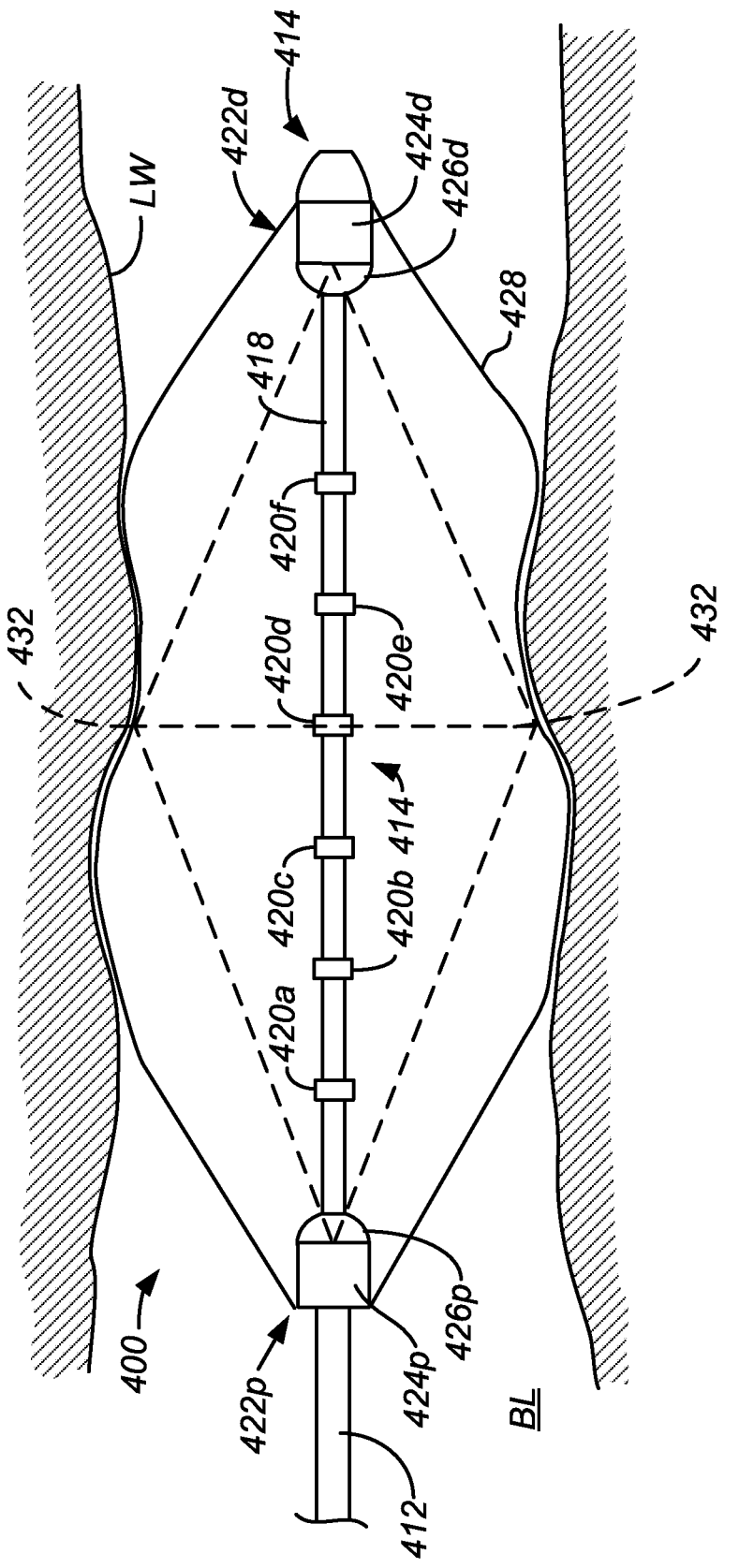
FIG. 4 illustrates a fourth embodiment of a catheter constructed in accordance with the principles of the present invention, where a plurality of fixed illumination sources are mounted between a pair of fixed light sensors within a balloon.

Referring now to FIG. 4, a catheter 400 represents a fourth embodiment of a catheter constructed in accordance with the principles of the present invention. Catheter 400 includes shaft 412 having a distal end 414 and a proximal end 416. A distal portion 418 of the catheter carries a plurality of fixed illumination sources 420a-420f distributed along its length. The illumination sources 420a-420f are located between a distal light sensor 422d and a proximal light sensor 422p and within a balloon 428. The light sensor 422d comprises a camera 424d and a lens 426d, and the light sensor 422p comprises a camera 424p and a lens 426p. Each of the illumination sources 420a-420f will usually be configured to project a ring-like light pattern 432, as illustrated for illumination source 420d. The illumination sources may all be illuminated simultaneously but will often be illuminated sequentially, allowing for the light sensors for 422d and 422p to triangulate the locations of the illumination points 432 sequentially as they become illuminated. The illumination sources 420a-420f may also be of different wavelengths and/or project distinct patterns if illuminated simultaneously.

Referring now to FIGS. 5A and 5B, a catheter 500 having a catheter shaft 512 with a distal end 514 and a proximal 516 is illustrated. The catheter 500 includes a single light sensor 522 attached at or near the distal end of the catheter shaft 512. As with previous embodiments, the light sensor 522 includes a camera 524 and a lens 526. A light-transmissive element 518 is attached to the distal end of the catheter shaft 512 and extends distally from the light sensor 522. The light transmissive element 518 will typically be formed from an optical wave guide material suitable for transmitting light from an illumination source 520 in a distal direction axially down the element of 518. A plurality of angled, partially reflective mirrors 550 are placed within the light-transmissive element 518 in order to perpendicularly (relative to a central axis of the catheter shaft 512) reflect a plurality light rings or other patterns along the luminal wall LW of the body lumen BL. Unlike previous embodiments, the catheter 500 does not include a balloon surrounding the illumination source 518. Thus, as some of the illuminated rings may not be visible from the light sensor 522, it will be relatively easy to reposition the catheter in the body lumen. Alternatively, the catheter 500 could be provided with an additional light sensor at the distal end (not illustrated) in order to allow more complete scanning of the interior of the blood vessel to detect the projected light patterns.

Figure 6A:
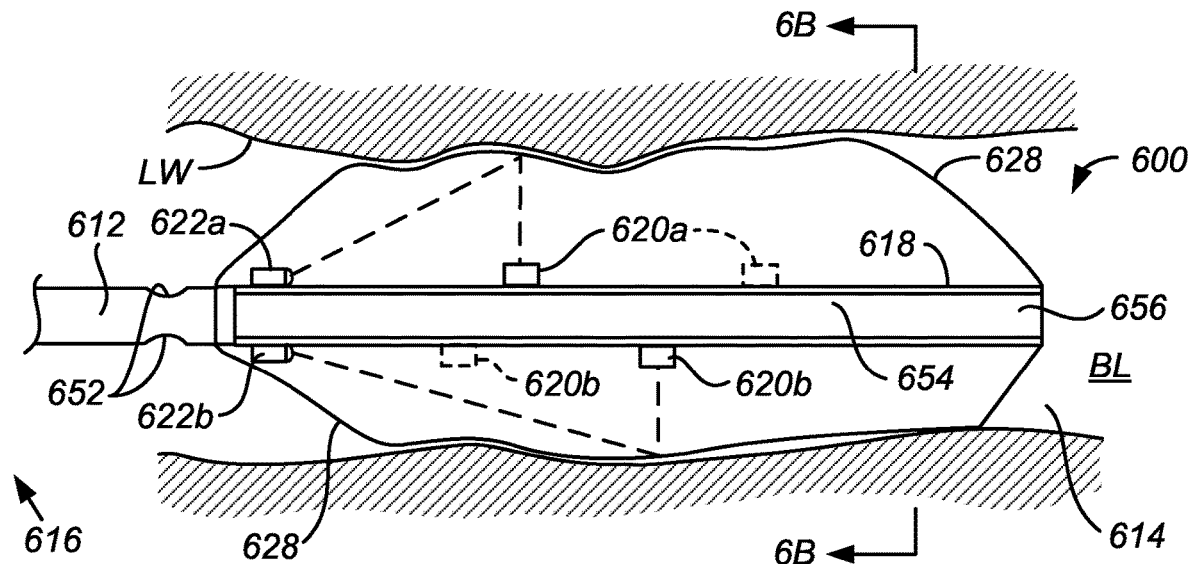
FIGS. 6A and 6B illustrate a sixth embodiment of a catheter constructed in accordance with the principles of the present invention with two or more illumination sources configured to axially translate on a distal portion of the catheter with two or more aligned light sensors, wherein the distal end of the catheter is configured to permit perfusion and the illumination sources and light sensors are within a balloon.
Figure 6B:
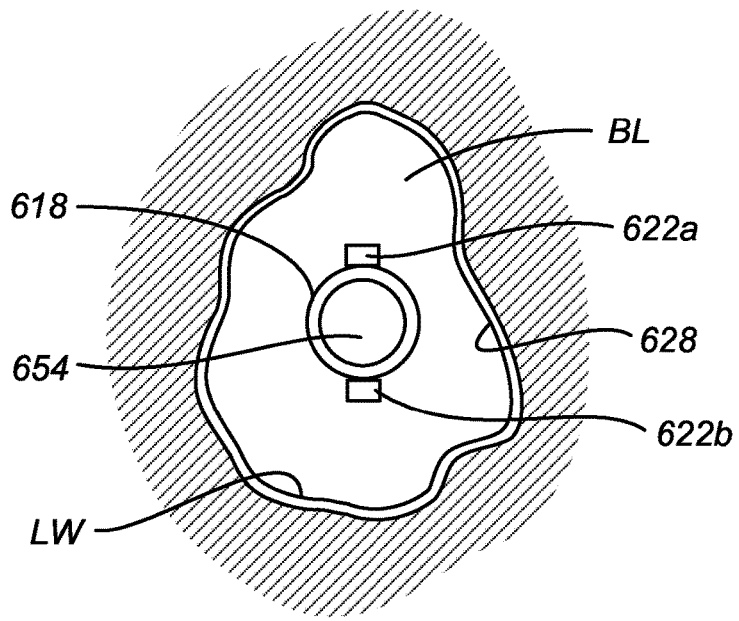

Referring now to FIGS. 6A and 6B, a catheter 600 representing yet a further embodiment of a catheter constructed in accordance with the principles of the present invention will be described. The catheter 600 includes a catheter shaft 612 having a distal end 614, a proximal end 616, and a distal portion 618. A pair of illumination sources 620a and 620b are configured to axially translate over an outer surface of the distal portion 618 of the catheter 600. Each of the illumination of sources 620a and 620b will be associated with at least one light sensor 622a and 622b, as illustrated. The illumination sources 620a and 620b will each typically project a partial light ring pattern, typically being somewhat more than a half ring pattern (i.e. extending over more than 180°), on the luminal wall so that the two partial ring patterns will overlap to circumscribe substantially the entire cross section of the lumen, and the light sensors 622a and 622b will be able to detect the light reflected when the partial light ring patterns strike the inner surface of balloon 628. Usually, one light sensor 622 is associated with each illumination source 620, but it will be appreciated that a second distally located light sensor could also be provided for each of the illumination sources. A particular advantage of the configuration of catheter 600 is that perfusion port 652 may be provided in the catheter shaft 612 in order to allow blood perfusion thru a perfusion lumen 654 and out through a perfusion port 656.

Figure 7A:
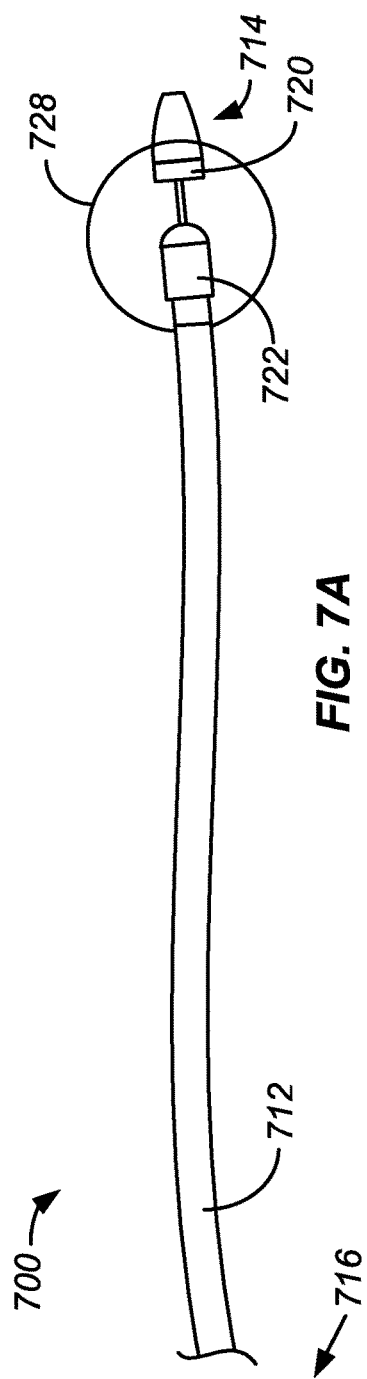
FIGS. 7A-7C illustrate a seventh embodiment of a catheter constructed in accordance with the principles of the present invention, where a single illumination source and single light sensor are fixedly mounted at the distal end of a catheter within a balloon, where the catheter is intended to be drawn through a body lumen in order to scan the luminal surface.
Figure 7B:
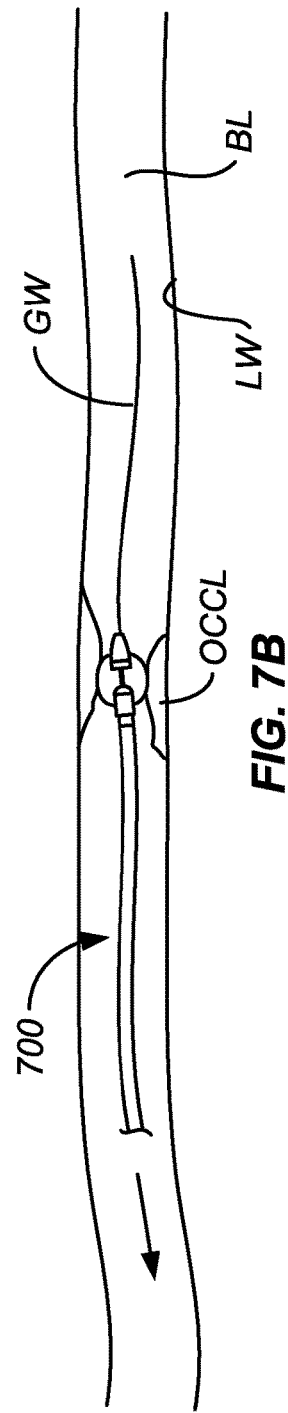
Figure 7C:
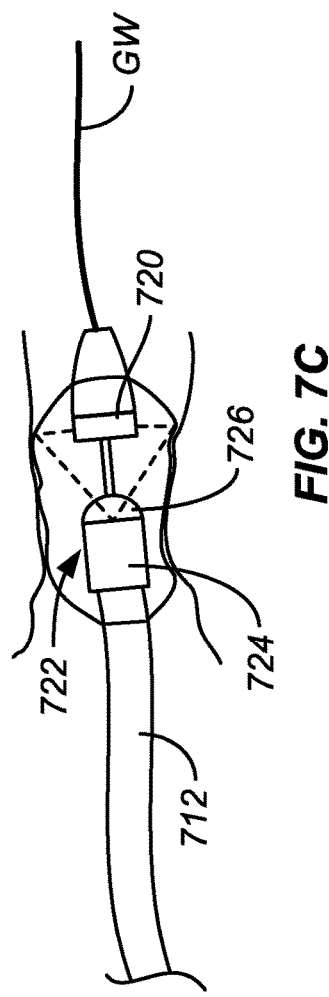

Referring now to FIGS. 7A-7C, a catheter 700 which represents yet a further embodiment of the present invention is shown to include a shaft 712 having a distal end 714 and a proximal end 716. An illumination source 720 and a light sensor 722 are fixedly mounted at the distal end of the catheter shaft 712 within an inflatable balloon 728. Neither the illumination source 720 nor the light sensor 722 are configured to translate on the catheter, and they are located relatively close to each other along the shaft 712 for a compact configuration. The catheter 700 will typically be deployed within the body lumen, usually a blood vessel, over a guide wire, so that the entire catheter 700 may be drawn or advanced through the body lumen BL in order to scan the luminal wall LW. The illumination source 720 will most typically project a ring pattern allowing the camera 724 and lens 726 of the light sensor 722 to measure the luminal dimensions as the catheter is being drawn through the lumen, as shown in FIG. 7C. It will be necessary, of course, for the system to track the axial location of the illumination source 720 and a light sensor 722 as they are translated through the body lumen. The system can optionally also be configured to track the position of the illumination source in embodiments where the balloon is stationary and the sensor and/or illumination source is moved inside the balloon. For example, the guidewire could be scaled with position markings or other detectable indicia (e.g. spaced-apart magnetic regions) that are read or detected by a sensor on the catheter as the catheter is drawn through the body lumen, Alternatively, Hall effect sensors could be employed or the imaging system could be configured to detect the rate of travel to allow tracking of the device position without additional hardware.

Figure 8:
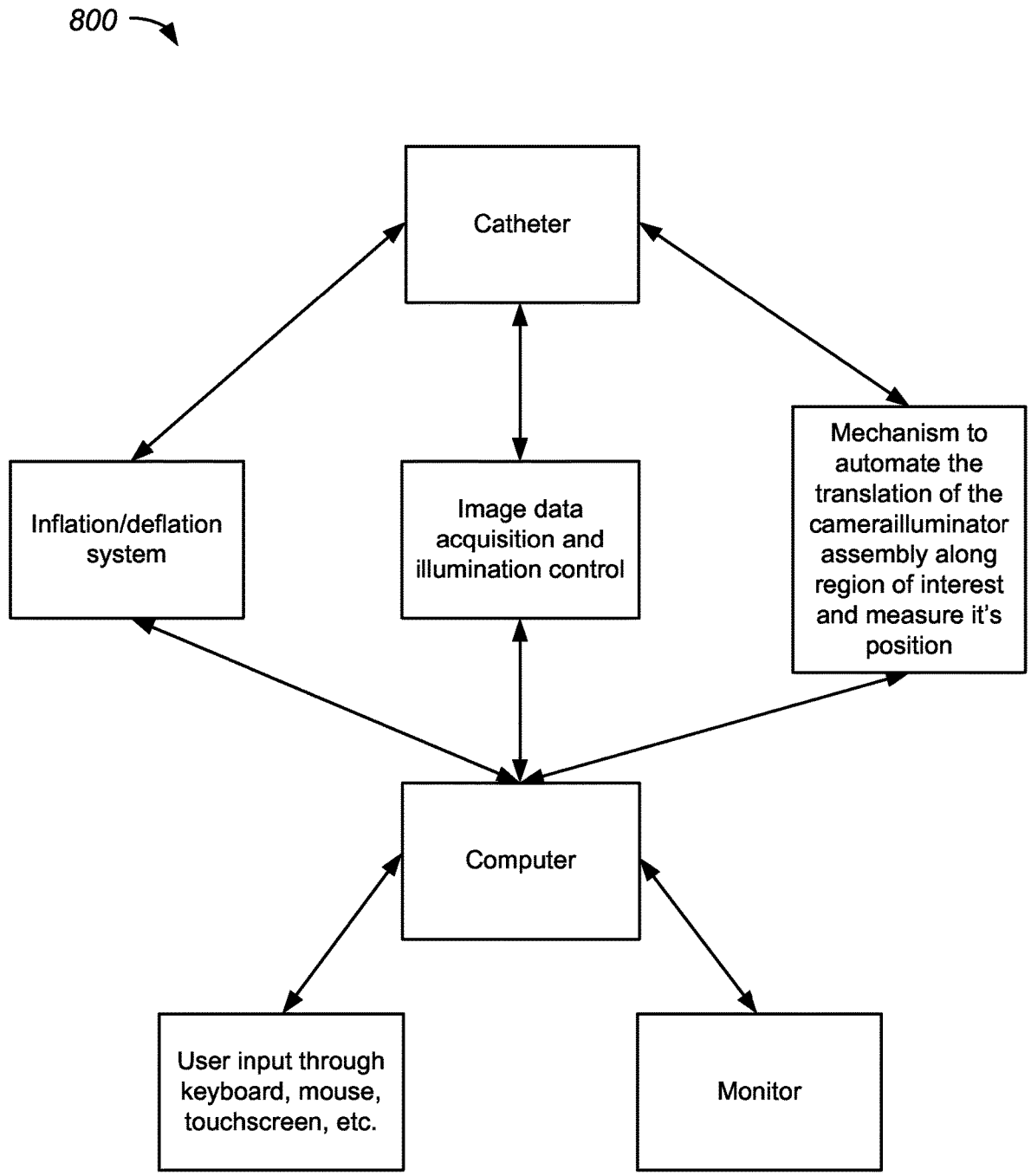
FIG. 8 is a schematic representation of systems of the present invention including the catheter and processor components suitable for performing the methods described herein.

Referring now to FIG. 8, any one of the catheters described previously may be employed in a system 800 which includes components which communicate with the catheter to gather data and provide calculations of the luminal dimensions. The system components will typically include both hardware components and software components. For example, the catheter will typically require an inflation and deflation system for inflating and deflating the balloon which surrounds the illumination and light sensing components. Hardware components will typically be needed in order to provide power for illumination and for advancing and retracting the illumination sources and/or light sensors on the catheter and determining their relative positions. Interfaces will also be needed in order to collect the analog and/or digital signals being generated by the light sensors, cameras, and the like. All of these hardware components will typically be linked to a computer or other processor, and the computer will typically include an interface, such as a touch screen, a keyboard, a mouse, voice activation, or the like, and a monitor or display.

Figure 9A:
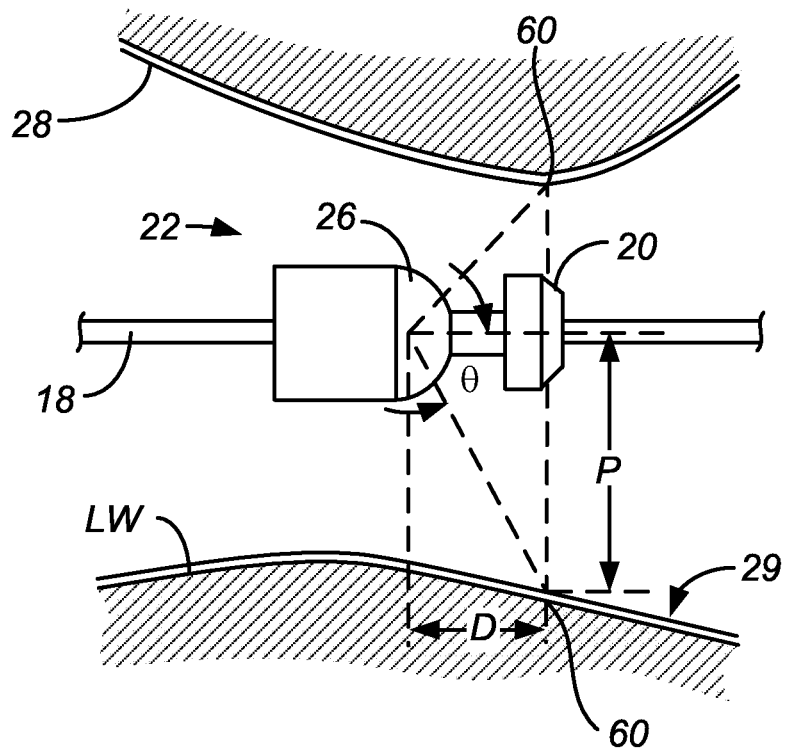
FIGS. 9A and 9B illustrate the principles of triangulation which allow measurement of the luminal diameters at various positions along the length of a body lumen.
Figure 9B:
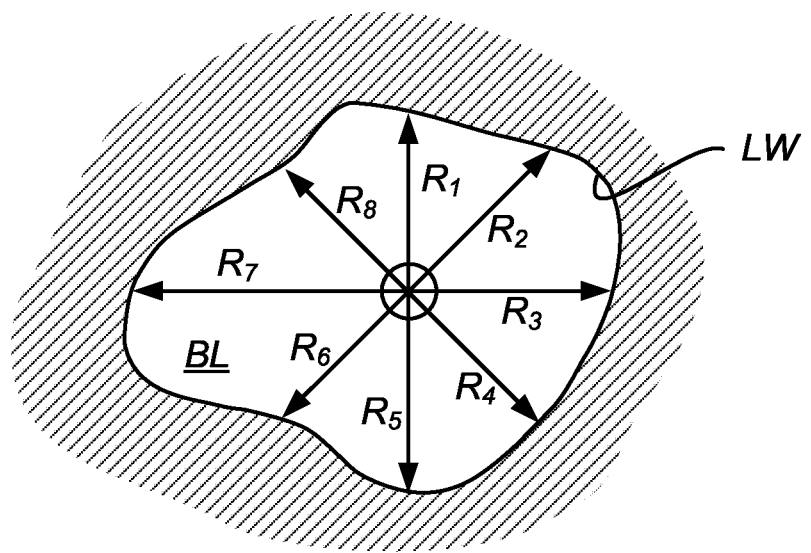

Referring now to FIGS. 9A and 9B, an exemplary calculation of a luminal radius R will be described. Using the catheter 10 of FIG. 1 as an example, the illumination source 20 projects a ring-like pattern over the inner wall of 29 of the balloon 28. The ring of light will illuminate a circumferential illumination line 60 which circumscribes a cross-section of the inner surface 29 of the balloon. The circumferential illumination line 60 will be detected by the light sensor 22 where the lens 26 focuses the incoming light on camera 24 which typically comprises a CCD, CMOS, or other conventional light sensor. Information from the camera is fed to a processor or other calculating system which can determine the incident angle $\theta$. The distance D between the illumination source 20 and the light sensor 422 is known. Thus, the radius R at any scanned point on the luminal surface may be calculated by the simple formula:

$$R = D \tan \theta$$

It will be appreciated that the radius R at all circumferential locations around the interior of the luminal wall LW may be determined, as shown in FIG. 9B, and that the measurements taken in FIG. 9B may be repeated incrementally at different axial locations with the body lumen. Thus, at the end of the procedure, a data matrix including the radial locations (in three dimensional space) of the illuminated points may be collected. This data matrix will be representative of the shape of the wall of the body lumen in the region that has been scanned.

Figure 10A:
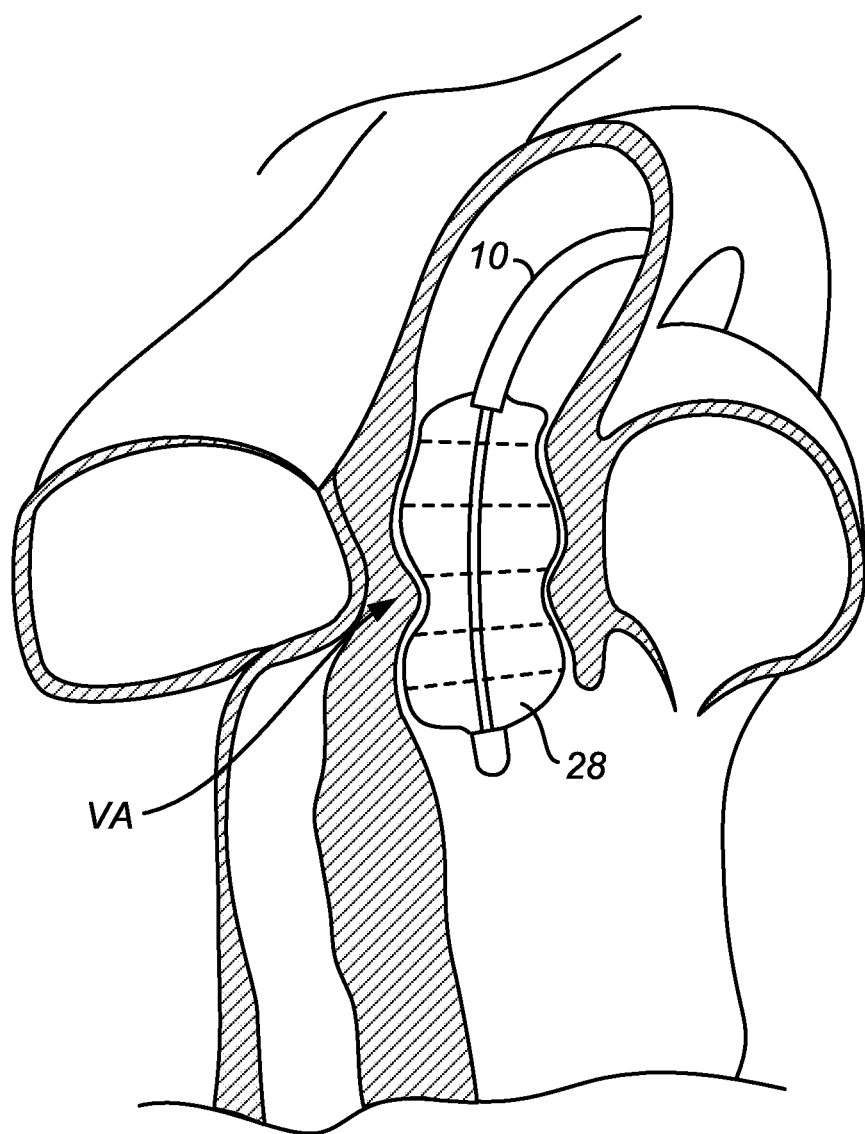
FIGS. 10A and 10B illustrate use of a catheter of the present invention in scanning and obtaining a digital topographic model of an aortic annulus in accordance with the principles of the present invention.
Figure 10B:
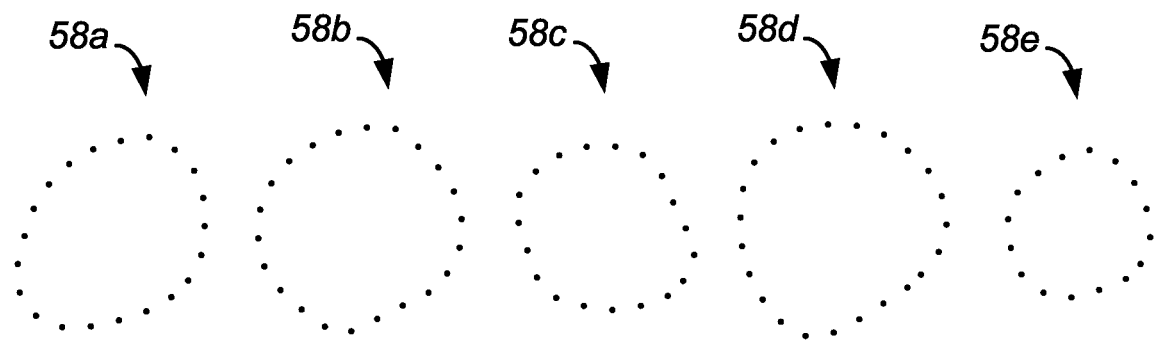
Figure 11:
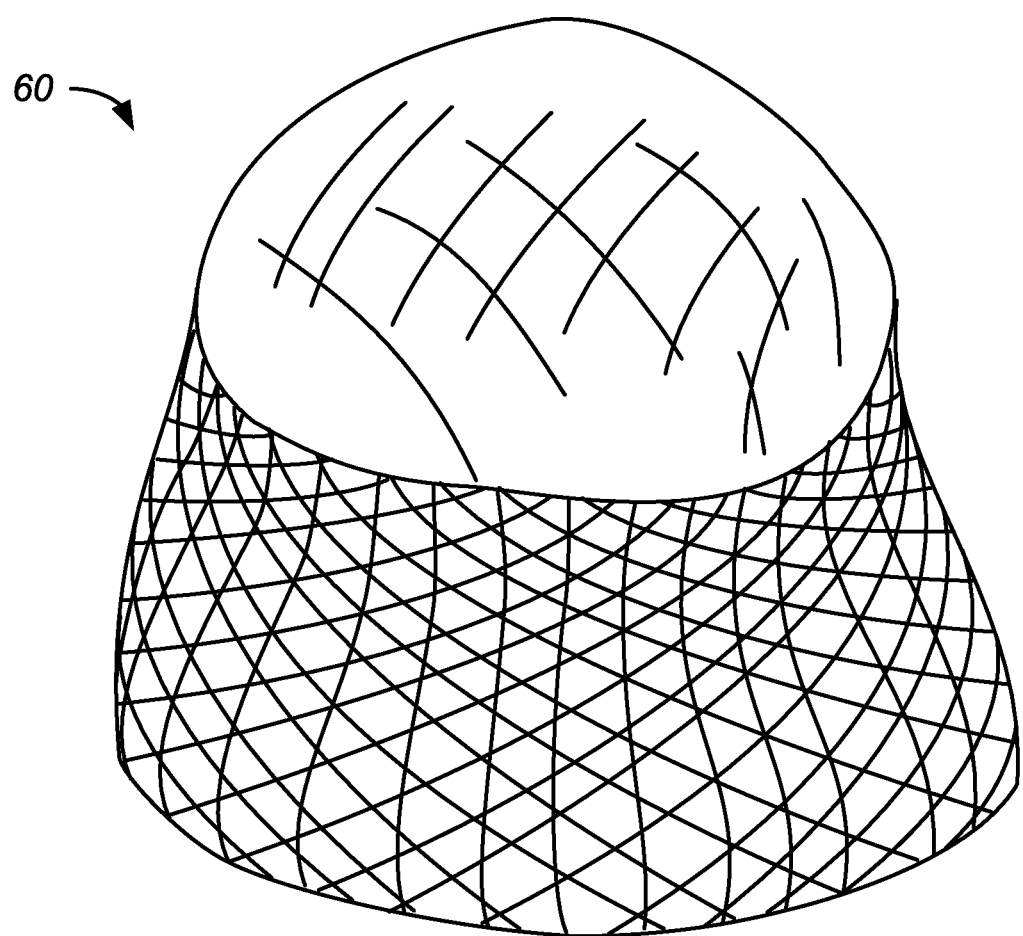
FIG. 11 illustrates an exemplary wire frame model of the type which might be provided by the methods of the present invention for use by a treating physician.

As shown in FIGS. 10A and 10B, the catheter 10 is placed in an aortic valve annulus VA and the body wall is scanned circumferentially at a number of axial locations. While scanning at five locations is illustrated, it will be appreciated that scanning will typically be performed at a much greater number of axial locations, typically at least 10, frequently at least 25, and often 100 or more. Scanning at each axial location results in multiple radial location points, as shown in FIG. 10B. As these data files are built up, it will be possible to generate not only precise quantitative dimensional information relating to the anatomical structure being scanned, but it will also be possible to produce highly accurate three dimensional images of the scanned luminal wall. For example, as shown in FIG. 11, a wire frame model 60 may be generated and displayed on the monitor or display screen. This image will be useful for many purposes including assisting in the selection of a prosthesis to be implanted. For example, digital, dimensionally correct models of the prosthesis may be displayed simultaneously on the monitor or display. The user may then manipulate the images to determine whether or not the prosthetic image is compatible with the dimensions of the luminal image. Moreover, as discussed above, by inflating a balloon to a pressure which corresponds to the expected outlook force generated by the prosthesis to be implanted, the dimensions of the fully expanded prosthesis can be compared with the expected deformed dimensions of the body lumen, making the comparison even more accurate.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A catheter for scanning a luminal surface of a body lumen to generate electronic signals useful for generating a digital topographic model of the luminal surface, said catheter comprising:
   a catheter shaft having a distal end, a proximal end, a distal portion with a straight axis, and a proximal portion, wherein the catheter shaft is configured to be advanced over a guidewire into the body lumen;
   at least one illumination source mounted on the distal portion of the catheter shaft, wherein the illumination source is configured to project an optical pattern comprising at least one ring encircling the distal portion of the catheter shaft in a plane which passes through the distal portion, and wherein the plane is disposed normal to the straight axis of the distal portion of the catheter shaft onto the luminal surface when the distal portion of the catheter shaft is in the body lumen; and
   at least one sensor mounted on the distal portion of the catheter shaft and axially spaced-apart from the at least one illumination source, wherein said at least one sensor is configured to sense light from the illumination source which has been reflected from the luminal surface and to produce an electronic signal representative of a reflected light pattern;
   whereby the digital topographic model can be generated by triangulation based on the projected optical pattern, a distance measured along the straight axis between the illumination source and the sensor, and the electronic signal.

2. A catheter as in claim 1, wherein the at least one illumination source is mounted to move axially over the distal portion of the catheter shaft.

3. A catheter as in claim 2, where the at least one illumination source moves over a distance in the range from 5 mm to 250 mm.

4. A catheter as in claim 2, wherein the at least one light sensor is coupled to the at least one illumination source so that the light sensor moves in tandem with the illumination source.

5. A catheter as in claim 2, wherein the at least one light sensor comprises a first light sensor mounted at a first fixed location on the distal portion of the shaft, wherein the first fixed location is axially spaced-apart from the at least one illumination source.

6. A catheter as in claim 5, wherein the at least one light sensor comprises a second light sensor mounted at a second fixed location on the distal portion of the shaft, wherein the second fixed location is axially spaced-apart from the at least one illumination source on a side opposite to that of the first fixed location.

7. A catheter as in claim 6, wherein a plurality of illumination sources is axially distributed over the straight axis of the distal portion of the shaft.

8. A catheter as in claim 7, wherein the plurality of illumination sources is distributed over a distance in a range from 5 mm to 250 mm.

9. A catheter as in claim 7, wherein the ring pattern circumscribes a cross-section of the lumen surrounding the illumination source.

10. A catheter as in claim 7, wherein at least some of the plurality of illumination sources project a pattern geometrically different from a pattern projected by one or more of the other illumination sources.

11. A catheter as in claim 10, wherein the illumination source and the light detector are both disposed within the balloon and the balloon is configured to be drawn through the body lumen to collect data from the reflected light.

12. A catheter as in claim 7, wherein at least some of the plurality of illumination sources project a pattern having a different light wavelength than projected by one or more other illumination sources.

13. A catheter as in claim 1, further comprising a balloon which is inflatable over the distal portion of the catheter shaft to isolate a region over the at least one illumination source and the at least one sensor.

14. A catheter as in claim 13, wherein the balloon is elastic.

15. A catheter as in claim 13, wherein the balloon is inelastic.

16. A catheter as in claim 13, wherein the balloon has a reflective interior surface.

17. A catheter as in claim 1, wherein the catheter shaft comprises a catheter body and at least a distal portion of the catheter body is transparent, wherein the illumination source and camera are disposed within said transparent distal portion of the catheter body.

18. A catheter as in claim 17, wherein the illumination source and camera are configured to move back and forth within said transparent distal portion of the catheter body.

19. A system comprising:
   the catheter as in claim 1; and
   a processor connected to receive the electronic signal and configured to generate the digital topographic model by triangulation based on the projected optical pattern and the distance between the illumination source and the sensor.

* * * * *